US00RE39157E

(19) United States
(12) Reissued Patent
Hess

(10) Patent Number: US RE39,157 E
(45) Date of Reissued Patent: Jul. 4, 2006

(54) APPARATUS FOR RESTENOSIS TREATMENT

(75) Inventor: Robert L. Hess, Portola Valley, CA (US)

(73) Assignee: Calmedica, LLC, Portola Valley, CA (US)

(21) Appl. No.: 08/850,073

(22) Filed: May 2, 1997

Related U.S. Patent Documents

Reissue of:
(64) Patent No.: 5,411,466
Issued: May 2, 1995
Appl. No.: 08/219,179
Filed: Mar. 28, 1994

U.S. Applications:
(63) Continuation of application No. 07/755,480, filed on Sep. 5, 1991, now Pat. No. 5,302,168.

(51) Int. Cl.
*A61N 5/00* (2006.01)

(52) U.S. Cl. ..... 600/3; 600/3; 606/7
(58) Field of Classification Search ..... 600/1–8; 606/7
See application file for complete search history.

(56) References Cited

U.S. PATENT DOCUMENTS

| | | | | | |
|---|---|---|---|---|---|
| 3,168,092 | A | * | 2/1965 | Silverman | |
| 3,324,847 | A | * | 6/1967 | Zoumboulis | 600/3 |
| 4,202,323 | A | * | 5/1980 | Zweig et al. | |
| 4,434,788 | A | * | 3/1984 | Nakatsugawa | |
| 4,588,395 | A | * | 5/1986 | Lemelson | |
| 4,697,575 | A | * | 10/1987 | Horowitz | |
| 4,733,665 | A | * | 3/1988 | Palmaz | |
| 4,815,449 | A | * | 3/1989 | Horowitz | |
| 4,878,492 | A | * | 11/1989 | Sinofsky | |
| 4,881,938 | A | * | 11/1989 | Van't Hooft | 600/3 |
| 5,019,075 | A | * | 5/1991 | Spears | |
| 5,059,166 | A | * | 10/1991 | Fischell et al. | |
| 5,084,002 | A | * | 1/1992 | Liprie | 600/3 |
| 5,213,561 | A | * | 5/1993 | Weinstein et al. | 600/3 |

* cited by examiner

*Primary Examiner*—John P. Lacyic
(74) *Attorney, Agent, or Firm*—Burns, Doane, Swecker & Mathis, LLP

(57) ABSTRACT

Method and apparatus for treatment and post-treatment of the stenosed region of an artery after reduction of the region by angioplasty or other means by applying a radioactive dose to said reduced region of the artery by positioning a radioactive dose to the reduced region is disclosed.

41 Claims, 4 Drawing Sheets

APPARATUS FOR RESTENOSIS TREATMENT

Matter enclosed in heavy brackets [ ] appears in the original patent but forms no part of this reissue specification; matter printed in italics indicates the additions made by reissue.

This application is a continuation of application Ser. No. 07/755,480, filed Sep. 5, 1991, now U.S. Pat. No. 5,302,168.

BACKGROUND OF THE INVENTION

This invention relates generally to angiop1asty and more particularly to a method and apparatus for preventing restenosis after angioplasty or other stenosis treatment.

BACKGROUND DESCRIPTION

In the past, catheters have been developed which may be effectively inserted into blood vessels and maneuvered through a vascular tree. A balloon may be used with such catheters to expand in the vessel and open blockages found therein. In a typical percutaneous transluminal coronary angioplasty (PTCA) or percutaneous transluminal angioplasty (PTA) procedure, a guiding catheter is percutaneously introduced into the vascular system of a patient through an artery and advanced therein until the distal tip of the guiding catheter is appropriately positioned. A dilation catheter having a balloon on the distal end thereof and a guide wire are slidably disposed and introduced through the guiding catheter. The guide wire is first advanced through the distal tip of the guiding catheter until the distal end of the guide wire crosses the lesion to be dilated. The dilation catheter is then advanced over the previously introduced guide wire until the dilation balloon on the distal extremity of the dilation catheter is properly positioned inside the lesion. The balloon portion of the dilation catheter is then inflated to a predetermined size to radially compress the atherosclerotic plaque of the lesion against the inside of the artery wall to thereby reduce the annular stenosed area. After a period of time, the balloon is deflated so that blood flow is resumed, allowing the dilation catheter to be removed.

A major problem encountered in a significant number of patients treated by this procedure is the subsequent narrowing of the artery after the expansion treatment. Various methods and apparatus have been developed to address the restenosis problem including multiple inflations of the balloon during the original procedure, atherectomy, hot balloons, and lasers. Even the installation of permanent stents has been thought to potentially have some value in reducing restenosis rates. See, for example, U.S. Pat. No. 5,019,075 to Spears et al. wherein the region surrounding the balloon utilized in the angioplasty procedure is heated by means within the balloon, or within the skin of the balloon, upon inflation of the balloon in order to ideally fuse together fragmented segments of tissue. U.S. Pat. No. 4,733,655 to Palmaz discloses an expansible vascular graft which is expanded within a blood vessel by an angioplasty balloon to dilate and expand the lumen of the blood vessel. The Palmaz method and apparatus leaves the expandable vascular graft in place to ideally prevent recurrence of stenosis in the body passageway.

However, recent data seems to indicate that the prior art methods described above do not significantly reduce restenosis rates of occurrence. In restenosis, a proliferation of cells following angioplasty is believed to cause the lesion to reform. The rate of occurrence of restenosis is generally considered to be about 33 percent. It would therefore be desirable to have a method and apparatus to treat a lesion in order to reduce the restenosis rate of occurrence. The present invention is believed to provide a unique method and apparatus to reduce the restenosis rate of occurrence following an angioplasty or like-intended procedure.

SUMMARY OF THE INVENTION

The purpose of the invention is to provide method and apparatus to significantly reduce restenosis rates of occurrence following an angioplasty procedure. To accomplish this purpose, there is provided method and apparatus for exposing the dilated lesion to a radiation dose that will affect smooth muscle cell growth. There is provided a catheter which has at its distal end a radioactive source, the source being maneuverable to the site of a lesion which has been dilated or removed, the apparatus allowing the site to be exposed to the radiation dose that will affect smooth muscle cells such that the rapid growth of such cells can be prevented, thereby controlling restenosis.

In one aspect of the invention there is provided a method for treatment and post-treatment of the stenosed region of an artery comprising the steps of:

reducing the annular stenosed area within an artery; and applying a radioactive dose to the area of reduced stenosis.

In another aspect of the invention there is provided a method for treatment and post-treatment of the stenosed region of an artery after reduction of said region by angioplasty or other means comprising the step of applying a radioactive dose to said reduced region of the artery.

In yet another aspect of the invention there is provided apparatus for post-treatment of a stenosed region of an artery that has been reduced by angioplasty or other means comprising:

radioactive dose means; and positioning means operatively connected to said dose means to position said dose means within the stenosed region of an artery that has been reduced by angioplasty or other means.

DESCRIPTION OF THE PREFERRED EMBODIMENTS

Figure 1:
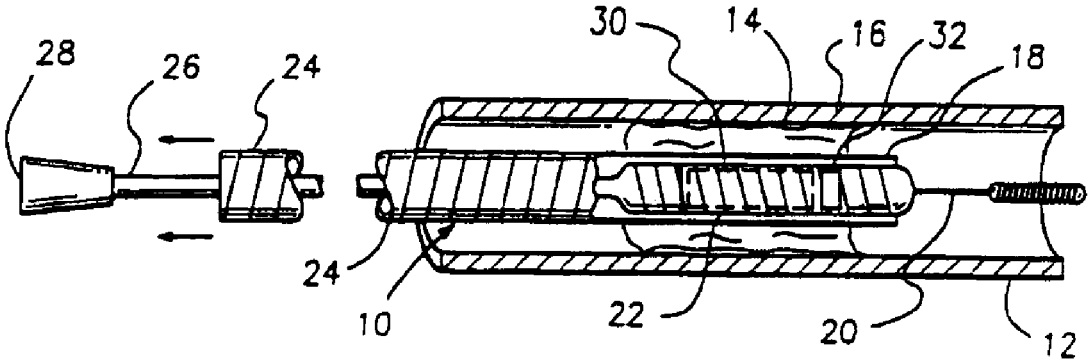
FIG. 1 is a partial cross-sectional view of an embodiment of the invention wherein said dose applying means is a radioactive element contained within a wire wound housing for radioactive containment, the housing having a window cut-out. A larger wire wound sheath covers the window during insertion and removal, the sheath being withdrawn to expose the radioactive element at the lesion site.

With continued reference to the drawing, FIG. 1 illustrates the apparatus and method for preventing restenosis of an artery that has been enlarged by angioplasty or other procedure. Specifically, apparatus, shown generally at 10, is positioned within artery segment 12 having lesion site 14 which has previously been enlarged by angioplasty or other procedure such that atherosclerotic plaque 16 has been radially compressed by expansion of the balloon portion of an angioplasty device (not shown) or removed by other means. Device 10 having distal end 18 with tip 20 and wire wound housing 22 is positioned such that housing 22 is positioned within the lesion site 14. Housing 22 contains radioactive dose means 30 and is provided with window cut-out 32. Device 10 includes a wire wound retractable sheath 24 and catheter shaft 26 with guide wire and guide wire port 28. A radioactive dose means 30 is moveable by advancing or retracting catheter shaft 26 which may be referred to as a positioning means. Sheath 24 is drawn back when the radioactive dose means is positioned directly proximate the lesion site 14 such that window cut-out 32 is opened to expose the lesion site 14, which has been previously dilated, to a radiation dose that will affect the smooth muscle cells/plaque.

Figure 2:
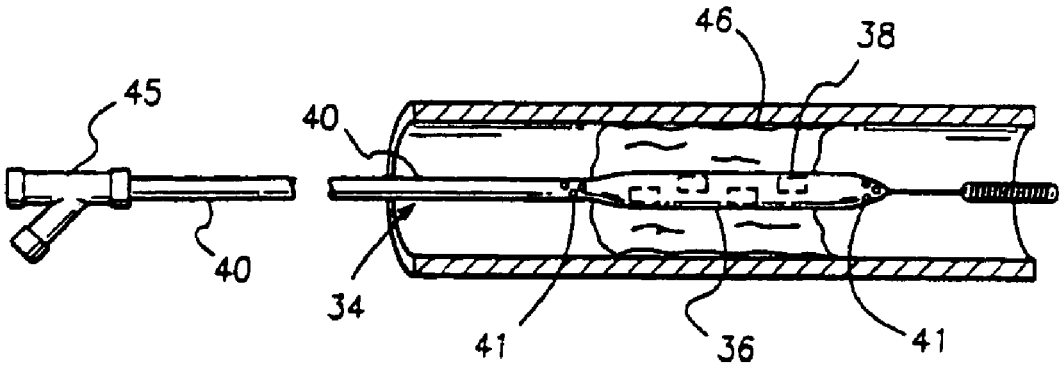
FIG. 2 is a partial perspective view of an alternate embodiment having a radioactive dose means positioned upon the balloon of an expandable balloon catheter, said balloon catheter being provided with a means or perfusion to allow blood flow during the time the balloon is inflated.

In FIG. 2 there is illustrated a device shown generally at 34 which is an alternate embodiment of the invention further including an angioplasty balloon 36 with dose means in the form of radioactive elements 38 attached thereto. Device 34 includes catheter shaft 40 having perfusion capabilities provided by holes 41 positioned proximately and distally to the balloon portion.

Figure 3:
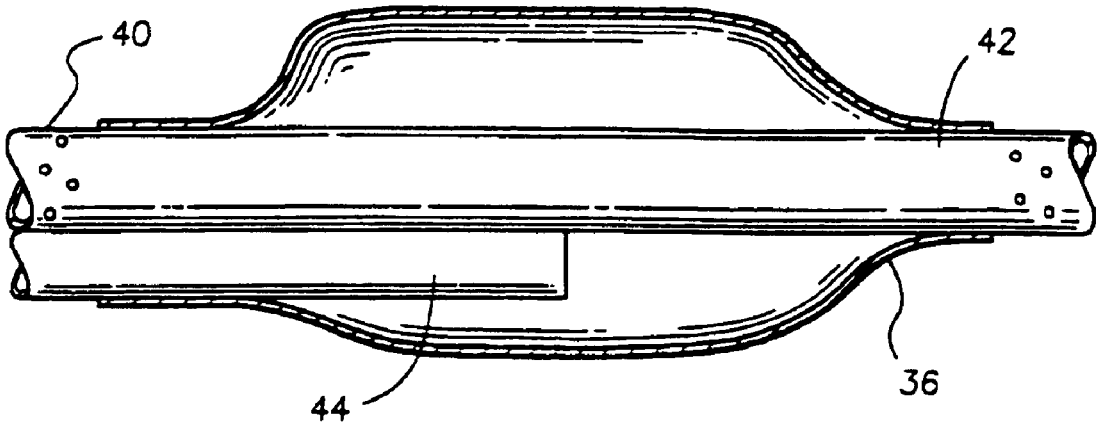
FIG. 3 is an enlarged partial cross-sectional view of a portion of the apparatus shown in FIG. 2.

FIG. 3 shows in expanded view details of balloon 36 of FIG. 2 positioned about catheter shaft 40 having two main lumens 42 and 44. Lumen 42 makes provision for guide wire capability and contains perfusion holes. Lumen 44 is the lumen which provides the passage to inflate the balloon from the inflation port 45 shown in FIG. 2 at the proximal end of the device 34. The radioactive elements 38 are not shown in FIG. 3.

Figure 4:
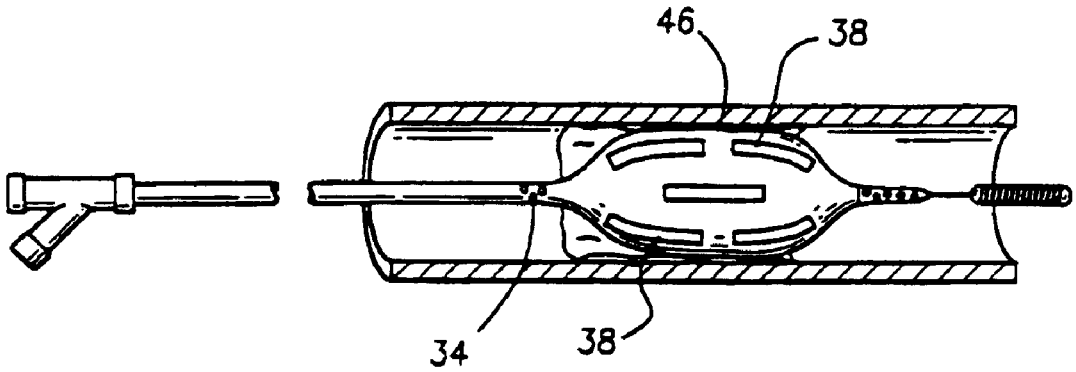
FIG. 4 is a partial perspective view of the apparatus shown in FIGS. 2 and 3 upon expansion of the balloon portion of the apparatus.

FIG. 4 illustrates the device 34 of FIGS. 2 and 3 wherein the balloon 36 is expanded in the vicinity of the lesion site 46, and the radioactive elements 38 are forced into contact with the lesion.

It is understood that the various embodiments of the subject invention are useful in the treatment of a lesion site within an artery. "Lesion site" includes those lesions which have been treated with balloon angioplasty, those lesions that have been treated by an atherectomy or laser angioplasty, those lesions that have been treated by rotational atherectomy or any other means of compressing or removing the material of the lesion which may cause trauma to the artery. It is this trauma which causes the proliferation of smooth muscle cells which method and apparatus of the subject invention is intended to inhibit.

With regard to all embodiments of the subject invention, "radioactive dose" means bombardment by particles emitted from radioactive materials including, but not limited to, materials such as Radon 222, Gold 198, Strontium 90, Radium 192, and Iodine 125. These materials may be incorporated into or delivered in a solid, liquid, or gaseous form, and the delivery of such forms is considered to be within the scope of the subject invention.

Figure 5:
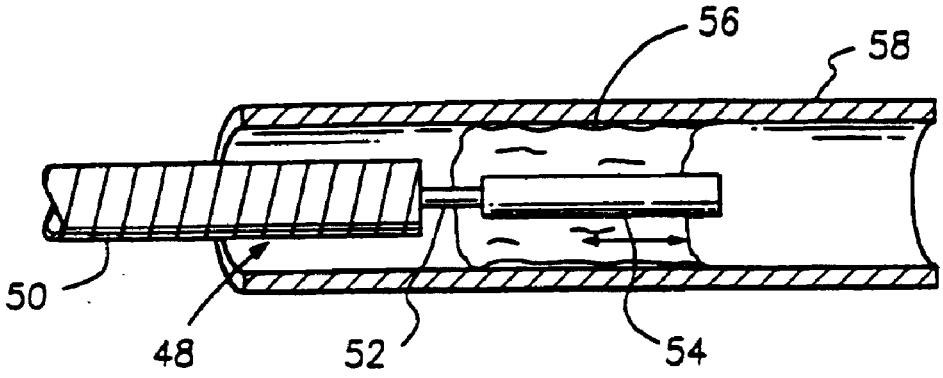
FIG. 5 is a partial perspective view of another embodiment of the invention wherein the radioactive dose means is an element that may be contained within a complementary containment means provided with a remotely actuated window.

FIG. 5 illustrates an alternate embodiment of the subject invention in the form of apparatus shown generally at 48. Sheath 50 of said device is preferably made from a helically wire wound member to provide a measure of shielding for the radioactive dose means. Device 48 includes positioning means 52 which is a motion wire providing slidable motion of the radioactive dose means 54 within the sheath. Radioactive dose means 54 is thus positionable proximate to the lesion site 56 of artery segment 58 *in a deployed configuration* and retractable within sheath 50 *in a non-deployed configuration* for insertion and removal within the artery segment 58.

Figure 6:
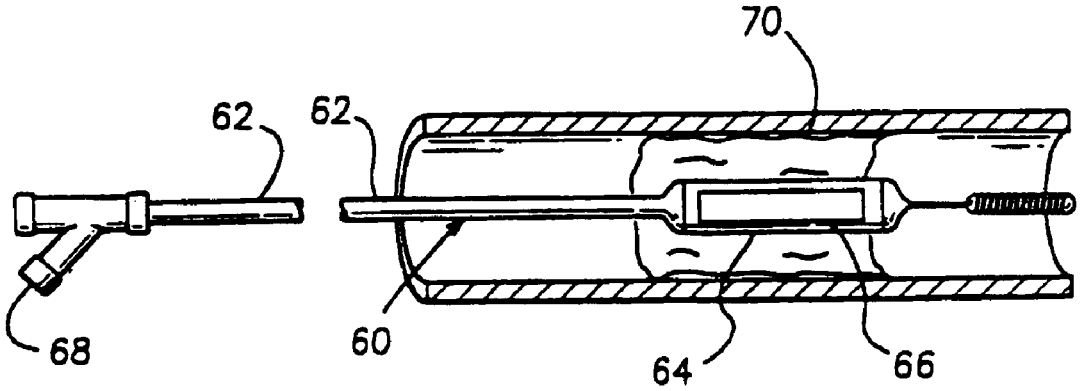
FIG. 6 is a partial perspective cross-sectional view of a catheter tip containing radioactive dose means showing the remotely actuated window.

FIG. 6 illustrates yet another embodiment of the subject invention in the form of the device shown generally at 60, similar to the device 10 shown in FIG. 1. In FIG. 6, device 60 is comprised of the shaft portion 62 and contains at its distal end a canister 64 containing the radioactive dose means. This canister 64 has a remotely actuated window 66 which can be actuated through port 68 to expose the radioactive dose means to the lesion 70.

Figure 7:
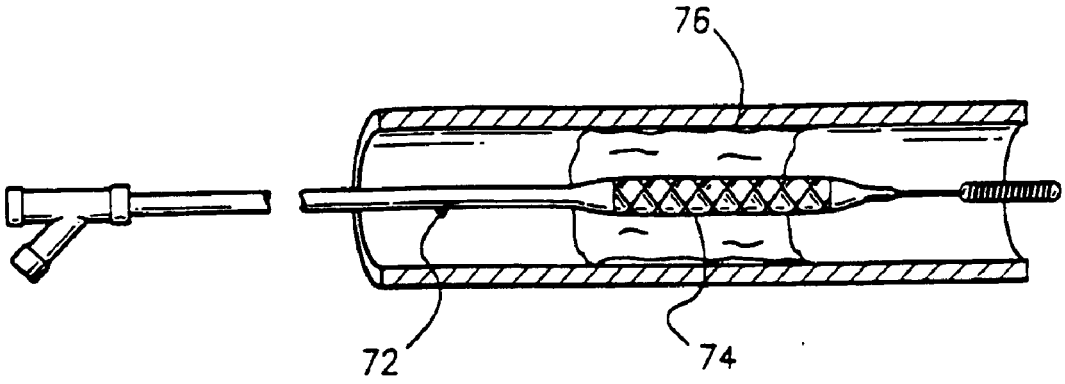
FIG. 7 is a partial perspective cross-sectional view of an alternate embodiment further including a stent wherein said radioactive dose means is in the form of a coating of radioactive material on the stent.
Figure 8:
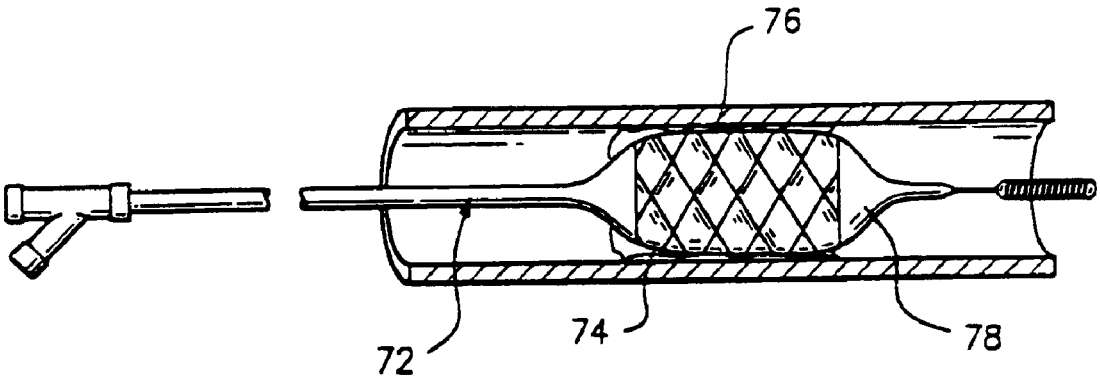
FIG. 8 is a partial cross-sectional view of the device shown in FIG. 7 after expansion of the stent shown in FIG. 7.
Figure 9:
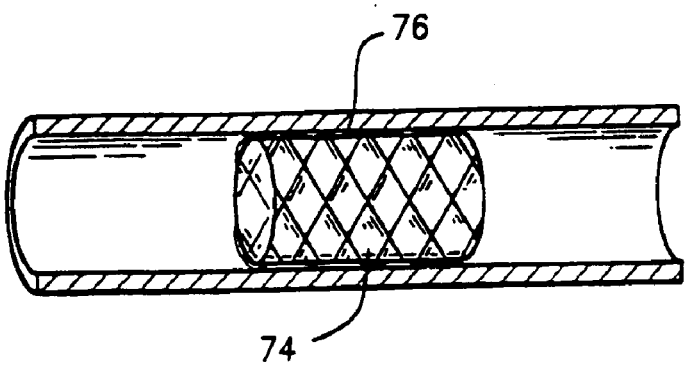
FIG. 9 is a partial perspective view of the stent illustrated in FIGS. 7 and 8 wherein the stent is implanted within the artery.

FIGS. 7, 8, and 9 illustrate yet another embodiment of the subject invention wherein a device shown generally at 72 is an inflatable stent delivery balloon system for delivery and expansion of stent 74. Stent 74 may be removable or may be a permanent implant. In the case of a permanently implanted stent, the radioactive dose means has to be carefully chosen in terms of dose level and half-life in order to limit the total radiation dose. In this embodiment, the radioactive dose means is associated with stent 74 and may be included as a cladding, a coating, an additive within the basic stent material itself, or an attachment by other means to the stent. In FIG. 7 the device 72 includes an inflatable balloon dilation catheter to position stent 74 within lesion 76.

FIG. 8 shows the expanded balloon of the stent delivery system 78 having dilated stent 74 in close proximal contact with lesion 76.

FIG. 9 shows the stent 74 in place within lesion 76 with the stent delivery system having been removed from the artery.

The foregoing description of the drawing illustrates various methods of the invention. It should be understood that the methods of the invention include the treatment and post-treatment of an annularly stenosed region of an artery. Most methods of treatment currently available cause some trauma to the artery. The artery in response to this trauma proliferates the growth of smooth muscle cells in many cases, and this results in restenosis at the site of the original stenosis—usually within a six-month period. The post-treatment consists of exposing the treated region of the stenosis to a radiation dose which is sufficient to retard or halt the proliferation of smooth muscle cells. It should also be pointed out that both the treatment and post-treatment could occur simultaneously if the device which removes or compresses the stenosis material also contains the radioactive dose means.

Having indicated above preferred embodiments of the present invention, it will occur to those skilled in the art that modification and alternatives can be practiced within the spirit of the invention. It is accordingly intended to define the scope of the invention only as indicated in the following claims.

What is claimed is:

1. Apparatus for post-treatment of stenosed region of an artery that has been reduced by angioplasty or other means comprising:

radioactive dose means for emitting radiation; and positioning means operatively connected to said dose means for advancing said dose means and positioning said dose means within the stenosed region of an artery that has been reduced by angioplasty or other means, said positioning means also being operatively connected to said dose means for withdrawing said dose means from the artery, the positioning means further including an angioplasty balloon, said radioactive dose means being connected to said balloon and moveable into contact with the stenosed region by expansion of said balloon.

2. The apparatus of claim 1, wherein the radioactive dose means comprises a plurality of radioactive sources distributed around the balloon.

3. Apparatus for post-treatment of stenosed region of an artery that has been reduced by angioplasty or other means comprising:

radioactive dose means for emitting radiation; and positioning means operatively connected to said dose means for advancing said dose means and positioning said dose means within the stenosed region of an artery that has been reduced by angioplasty or other means, said positioning means also being operatively connected to said dose means for withdrawing said dose means from the artery, the positioning means including a retractable sheath which may be removably positioned over said radioactive dose means and the dose means being located in a housing having a cut-out in a sidewall thereof, the dose means being exposed to the stenosed region by moving the sheath from a first position wherein the cut-out is covered by the sheath to a second position wherein the cut-out is not covered by the sheath.

4. The apparatus of claim 3, wherein the housing is a wirewound housing.

5. Apparatus for post-treatment of stenosed region of an artery that has been reduced by angioplasty or other means comprising:

radioactive dose means for emitting radiation; and positioning means operatively connected to said dose means for advancing said dose means and positioning said dose means within the stenosed region of an artery that has been reduced by angioplasty or other means, said positioning means also being operatively connected to said dose means for withdrawing said dose means from the artery, the positioning means including a retractable remotely activated cover which may be removably positioned over said radioactive dose means and the dose means being located in a housing having an opening therein, the dose means being exposed to the stenosed region by moving the remotely activated cover from a first position wherein the opening is covered by the remotely activated cover to a second position wherein the opening is not covered by the remotely activated cover.

*6. Apparatus for post-treatment of a stenosed region of an artery that has been reduced by angioplasty or other procedure comprising:*

*a radioactive dose for emitting radiation;*

*a catheter; and*

*a positioner providing slidable motion of the radioactive dose within the catheter, the positioner arranged for advancing said dose within the stenosed region of an artery that has been reduced by angioplasty or other procedure, said positioner also being operatively connected to said dose for positioning the dose between a first position and a second position, wherein in the first position the dose is positioned within the artery in a non-deployed configuration and a second position wherein the dose is in a deployed configuration and exposed through a window in the catheter for treating at least a portion of the stenosed region of the artery, said positioner being operatively connected to said dose for withdrawing said dose from the artery after said radioactive dose is exposed to the stenosed region for a period of time sufficient to inhibit restenosis of the stenosed region.*

*7. The apparatus of claim 6, wherein the dose is in solid form.*

*8. The apparatus of claim 6, wherein the dose is in liquid form.*

*9. The apparatus of claim 6, wherein the dose is in gaseous form.*

*10. Apparatus for post treatment of a stenosed region of an artery that has been reduced by angioplasty or other procedure comprising:*

*a radiation source; and*

*a catheter having at least one lumen adapted to deliver said radiation source within the stenosed region of an artery that has been reduced by angioplasty or other procedure, said catheter also being adapted to at least partially reposition relative to the radiation source for treatment when positioned within the stenosed region of an artery, the catheter being adapted to at least partially reposition to withdraw said radiation source from the artery after said radiation source is exposed to the stenosed region for a period of time sufficient to inhibit restenosis of the stenosed region.*

*11. The apparatus of claim 10, wherein the radiation source is in solid form.*

*12. The apparatus of claim 10, wherein the radiation source is in a liquid form.*

*13. The apparatus of claim 10, wherein the radiation source is in gaseous form.*

*14. The apparatus of claim 10, wherein the catheter includes a balloon, the catheter defining at least one hole distal to the balloon and at least one hole proximal to the balloon.*

*15. The apparatus of claim 14, wherein the catheter includes a first lumen in fluid communication with the balloon.*

*16. The apparatus of claim 15, wherein the catheter defines a plurality of perfusion holes and includes a second lumen in fluid communication with perfusion holes which allow perfusion of blood in the artery during inflation of the balloon.*

*17. The apparatus of claim 10, wherein the radiation source provides a radiation dose to the stenosed region through a window in the catheter.*

*18. The apparatus of claim 10, wherein the catheter includes a balloon inflated by a fluid having the radiation dose means incorporated therein.*

*19. The apparatus of claim 6, wherein the radioactive dose for emitting radiation is positioned within the catheter, the catheter defining a housing, wherein in the first position the dose is shielded from treating the stenosed region and in the second position the housing is deployed to at least partially expose the dose to the stenosed region of the artery.*

*20. The apparatus of claim 19, wherein in the second deployed position a sheath is withdrawn relative to the dose positioned in the stenosed region to expose the stenosed region to the dose.*

*21. The apparatus of claim 10, wherein the catheter includes a balloon with the radiation source for emitting radiation incorporated into and enclosed within the material of the balloon and the balloon is expanded in the second deployed configuration positioning the balloon at least partially in contact with the stenosed region of the artery.*

*22. The apparatus of claim 21, wherein the portion of the device that is expanded includes a balloon with the radiation source positioned on the surface of the balloon.*

*23. The apparatus for post-treatment of a stenosed region of claim 17, wherein the dose is a liquid.*

*24. The apparatus for post-treatment of a stenosed region of claim 17, wherein the dose is a gas.*

*25. The apparatus for post-treatment of a stenosed region of claim 21, wherein the dose incorporated into the balloon material is a solid.*

*26. The apparatus for post-treatment of a stenosed region of claim 21, wherein the dose incorporated into the balloon material is a liquid.*

*27. The apparatus for post-treatment of a stenosed region of claim 21, wherein the dose incorporated into the balloon material is a gas.*

*28. The apparatus for post-treatment of a stenosed region of claim 6, wherein the apparatus controls the exposure of the dose by controlling the radial direction and axial position of the window.*

*29. Apparatus for post-treatment of a stenosed region of an artery that has been reduced by angioplasty or other procedure comprising:*

*a radioactive dose for emitting radiation;*

*a catheter movable with respect to the dose; and*

*a positioner configured to advance said catheter and dose within of an artery that has been reduced by angioplasty or other procedure, said positioner also configured to position the catheter and dose between a first position and a second position, wherein in the first position the dose is positioned within the artery in a non-deployed configuration and a second position wherein the dose is in a deployed configuration and exposed through a window in the catheter for treating at least a portion of the stenosed region of the artery, said positioner configured to withdraw said catheter and dose from the artery after said radioactive dose is exposed to the stenosed region for a period of time sufficient to inhibit restenosis of the stenosed region.*

*30. The apparatus of claim 29, wherein the dose is in solid form.*

*31. The apparatus of claim 29, wherein the dose is in liquid form.*

*32. The apparatus of claim 29, wherein the dose is in gaseous form.*

*33. The apparatus of claim 29, wherein the radioactive dose for emitting radiation is positioned within the catheter, the catheter defining a housing, wherein in the first position the dose is shielded from treating the stenosed region and in the second position the housing is deployed to at least partially exposed the dose to the stenosed region of the artery.*

*34. The apparatus of claim 33, wherein in the second deployed position the catheter is withdrawn relative to the dose positioned in the stenosed region to expose the stenosed region to the dose.*

*35. Apparatus for post-treatment of a stenosed region of an artery that has been reduced by angioplasty or other procedure comprising:*

*a radioactive dose for emitting radiation, wherein the radioactive dose is incorporated into a liquid for delivery;*

*a catheter; and*

*a positioner providing slidable motion of the radioactive dose within the catheter, the positioner arranged for advancing said dose within the stenosed region of an artery that has been reduced by angioplasty or other procedure, said positioner also being operatively connected to said dose for positioning the dose between a first position and a second position, wherein in the first position the dose is positioned within the artery in a non-deployed configuration and a second position wherein the dose in in a deployed configuration for treating at least a portion of the stenosed region of the artery, said positioner being operatively connected to said dose for withdrawing said dose from the artery after said radioactive dose is exposed to the stenosed region for a period of time sufficient to inhibit restenosis of the stenosed region.*

*36. The apparatus of claim 10, wherein the radiation source is incorporated into a liquid for delivery.*

*37. Apparatus for post-treatment of a stenosed region of an artery that has been reduced by angioplasty or other procedure comprising:*

*a radioactive dose for emitting radiation, wherein the radioactive dose is incorporated into a liquid for delivery;*

*a catheter movable with respect to the dose; and*

*a positioner configured to advance said catheter and dose within of an artery that has been reduced by angioplasty or other procedure, said positioner also configured to position the catheter and dose between a first position and a second position, wherein in the first position the dose is positioned within the artery in a non-deployed configuration and a second position wherein the dose is in a deployed configuration for treating at least a portion of the stenosed region of the artery, said positioner configured to withdraw said catheter and dose from the artery after said radioactive dose means is exposed to the stenosed region for a period of time sufficient to inhibit restenosis of the stenosed region.*

*38. Apparatus for post-treatment of a stenosed region of an artery that has been reduced by angioplasty or other procedure comprising:*

*a radioactive dose for emitting radiation;*

*a catheter for delivering the radioactive dose to and removing the radioactive dose from the stenosed region of an artery that has been reduced by angioplasty or other procedure; and*

*a positioner configured to move the catheter and the radioactive dose with respect to one another to move the radioactive dose from a non-deployed and shielded position to a deployed and unshielded position, wherein the dose is exposed through a window in the catheter for a period of time sufficient to inhibit restenosis of the stenosed region.*

*39. Apparatus for post-treatment of a stenosed region of an artery that has been reduced by angioplasty or other procedure comprising:*

*a radioactive dose for emitting radiation, wherein the radioactive dose is incorporated into a liquid for delivery;*

*a catheter for delivering the radioactive dose to and removing the radioactive dose from the stenosed region of an artery that has been reduced by angioplasty or other procedure; and*

*a positioner configured to move the catheter and the radioactive dose with respect to one another to move*

*the radioactive dose from a non-deployed and shielded position to a deployed and unshielded position for a period of time sufficient to inhibit restenosis of the stenosed region.*

*40. The apparatus of claim 10, wherein the radiation source provides a radiation dose to the stenosed region through a window in the catheter.*

*41. Apparatus for treatment of a lesion site in an artery with radiation comprising:*

*a radioactive dose for emitting radiation, wherein the radioactive dose is incorporated into a liquid for delivery;*

*a catheter for delivering the radioactive dose to and removing the radioactive dose from the lesion site in the artery that has been reduced by angioplasty or other procedure; and*

*a positioner configured to move the catheter and the radioactive dose with respect to one another to move the radioactive dose from a non-deployed and shielded position to a deployed and unshielded position for a period of time sufficient to inhibit restenosis of the lesion site.*

* * * * *